US012655391B2

(12) United States Patent
Tran et al.

(10) Patent No.: US 12,655,391 B2
(45) Date of Patent: Jun. 16, 2026

(54) MODIFIED K562 FEEDER CELL LINE EXPRESSING FACTORS THAT ENHANCE THE ACTIVATION AND PROLIFERATION OF NATURAL KILLER CELLS AND A METHOD FOR ITS PRODUCTION

(71) Applicant: Le Son Tran, Ho Chi Minh (VN)

(72) Inventors: Le Son Tran, Ho Chi Minh (VN); Thi Bao Tram Tran, Ho Chi Minh (VN); Thi Van Anh Bui, Kien Giang (VN)

(73) Assignee: GENE SOLUTIONS JOINT STOCK COMPANY, Ho Chi Minh city (VN)

( * ) Notice: Subject to any disclaimer, the term of this patent is extended or adjusted under 35 U.S.C. 154(b) by 0 days.

(21) Appl. No.: 19/064,618

(22) Filed: Feb. 26, 2025

(65) Prior Publication Data

US 2025/0333700 A1 Oct. 30, 2025

Related U.S. Application Data

(60) Provisional application No. 63/558,654, filed on Feb. 28, 2024.

(51) Int. Cl.
| | |
|---|---|
| *C12N 5/0783* | (2010.01) |
| *A61K 40/15* | (2025.01) |
| *A61K 40/31* | (2025.01) |
| *C12N 15/86* | (2006.01) |

(52) U.S. Cl.
CPC ............ *C12N 5/0646* (2013.01); *A61K 40/15* (2025.01); *A61K 40/31* (2025.01); *C12N 15/86* (2013.01); *C12N 2502/30* (2013.01); *C12N 2510/00* (2013.01); *C12N 2740/15043* (2013.01)

(58) Field of Classification Search
CPC .. C12N 5/0646; C12N 15/86; C12N 2502/30; C12N 2510/00; C12N 2740/15043; A61K 40/15; A61K 40/31
See application file for complete search history.

(56) References Cited

U.S. PATENT DOCUMENTS

| | | | |
|---|---|---|---|
| 2017/0239297 A1 * | 8/2017 | Günther ................. | A61K 40/10 |
| 2022/0325245 A1 * | 10/2022 | Rezvani ................. | A61P 35/00 |
| 2022/0372442 A1 * | 11/2022 | Jang ........................ | C07K 14/55 |

FOREIGN PATENT DOCUMENTS

| | | | | |
|---|---|---|---|---|
| CN | 110964698 A | * | 4/2020 | .............. A61P 35/00 |
| CN | 111518834 A | * | 8/2020 | ......... A61K 39/0011 |
| CN | 112779215 A | * | 5/2021 | ........... C12N 5/0646 |
| CN | 115261318 A | * | 11/2022 | .............. A61P 31/00 |

OTHER PUBLICATIONS

Ghani et al., Human Gene Therapy, 2009, 20:966-974.*
Portillo et al., Star Protocols, 2021, 2, 100596, pp. 1-24.*
Ludwig et al, Cell Systems, Jun. 2023, 14: 482-500, e1-e8.*

* cited by examiner

*Primary Examiner* — Hong Sang

(57) ABSTRACT

A method for generating or expanding a population of natural killer cells (NK cells) via using modified K562 feeder cells having expression of factors capable of increasing activation and proliferation of natural killer cells, wherein the factors capable of increasing activation and proliferation of NK cells include: (A) a co-stimulatory molecule comprises CD80 molecules, and 4-1BBL molecules; and (B) a cytokine, specifically membrane-bound IL-21 (mbIL-21).

2 Claims, 12 Drawing Sheets

Specification includes a Sequence Listing.

FIG. 2A                                        FIG. 2B

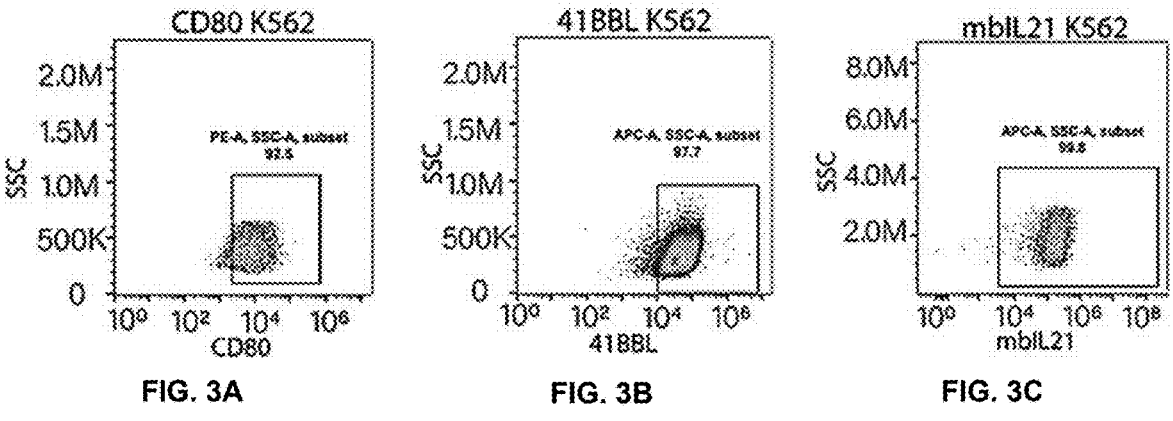
FIG. 3A          FIG. 3B          FIG. 3C
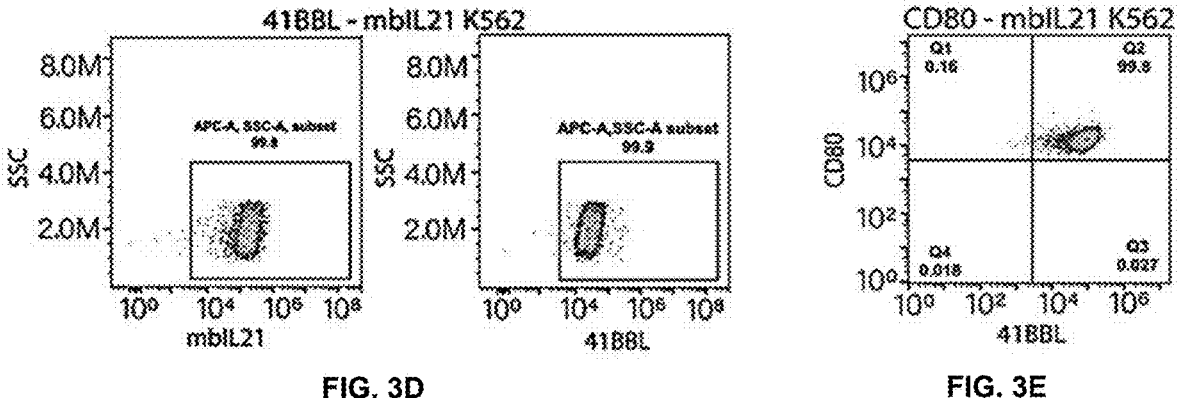
FIG. 3D                    FIG. 3E
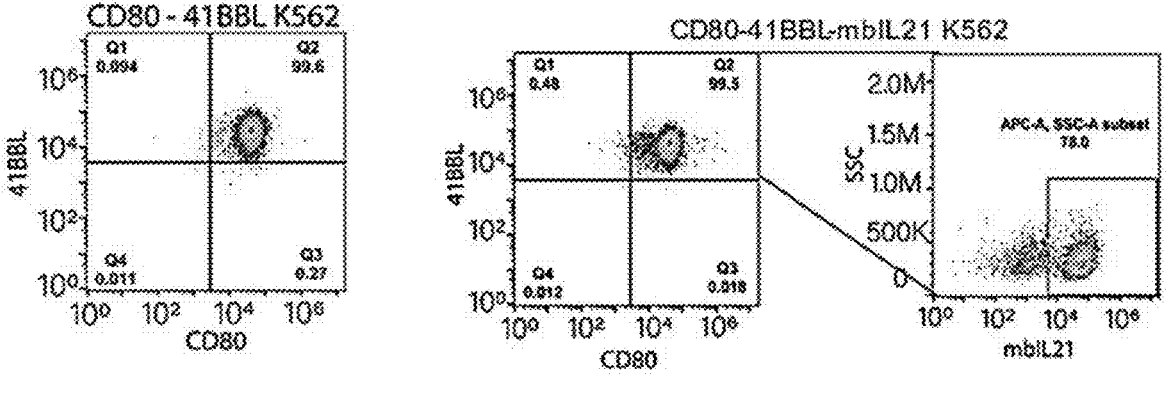
FIG. 3F                    FIG. 3G

MODIFIED K562 FEEDER CELL LINE EXPRESSING FACTORS THAT ENHANCE THE ACTIVATION AND PROLIFERATION OF NATURAL KILLER CELLS AND A METHOD FOR ITS PRODUCTION

CLAIM OF PRIORITY

This application claims the benefit of the U.S. Provisional Application Ser. No. 63/558,654, entitled "A modified K562 feeder cell line expressing factors that enhance the activation and proliferation of natural killer cells and a method for its production", filed on Feb. 28, 2024. The patent application identified above is incorporated here by reference in its entirety to provide continuity of disclosure.

FIELD OF THE INVENTION

The present invention pertains to the field of immunology and medicine, specifically addressing the purification and proliferation culture of natural killer cells isolated from cord blood. Natural killer (NK) cells play a crucial role in immune defense by targeting virus-infected cells, tumors, and other cellular abnormalities. More specifically, this invention focuses on modified K562 feeder cells expressing factors that enhance the activation and proliferation of natural killer cells, along with a method for their production.

INCORPORATION BY REFERENCE OF MATERIAL SUBMITTED ELECTRONICALLY

This application contains, as a separate part of disclosure, a sequence listing in computer-readable form (filename: GENS_006_Seqlisting.xml; size: 4,555 bytes; created Feb. 7, 2025) which is submitted via Patent Center in XML format in compliance with 37 CFR 1.831-1.835, and is incorporated by reference in its entirety.

BACKGROUND ART

Recognized for their rapid response and direct cytotoxicity, natural killer (NK) cells play a pivotal role in the innate immune system. In the malignant context, NK cells demonstrate the ability to identify stressed cells, irrespective of neoantigen presentation and those that have lost expression of MHC class I. This unique capability positions NK cells as a potent resource for cancer immunotherapy. The incorporation of NK cells into cell-based therapy has emerged as a novel and promising addition to the arsenal of cancer therapeutics.

Unlike T cells, the adoptive transfer of NK cells does not lead to severe toxicities induced by cytokine release syndrome or graft-versus-host reactions, providing a potential off-the-shelf solution for cell-based therapy in cancer treatment that can be obtained from allogeneic sources. An essential challenge in this field is the mass production of NK cells with cytotoxicity for clinical efficacy. In adult peripheral blood, NK cells constitute only 10-15% of lymphocytes; this percentage can reach up to 30% in cord blood. Distinct phenotypes can be observed in NK cells collected from each source. For instance, cord-blood NK cells can exhibit an immature phenotype with milder cytotoxicity, associated with low expression of CD16, in contrast to those from peripheral blood. NK cells purified from either source can be expanded in vitro using feeder-free or feeder-dependent methods. Feeder-free methods rely on the combination of cytokines such as IL-2, IL-15, IL-21, or IL-12 and IL-18 to induce a memory phenotype. NK cells expanded through this approach are reported to have high cytotoxicity, although the resulting fold expansion is limited. On the contrary, feeder-dependent methods often yield more robust expansion, reaching up to over 40,000-fold expansion. In these methods, NK cells are co-cultured with irradiated feeder cells engineered to express common ligands for co-stimulatory receptors such as 4-1BBL, OX40L or a membrane-bound cytokine such as IL-15 and IL-21.

Recognized as a co-stimulatory molecule, CD80 provides a crucial costimulatory signal to T cells upon its transient expression on B cells, macrophages and dendritic cells. The support is crucial for the activation of the T cells through the recognition of presented antigens via the T cell receptor (TCR). The co-stimulatory signal helps sustain T cell responses, enhances their survival, and promotes cytokine production. The presence of CD80 in the tumor microenvironment plays an important role in tumor immune surveillance. The expression of CD80 on tumor cells can enhance recognition by NK cells, leading to tumor lysis.

Several studies have investigated the triggering effect of CD80 on NK cells. Previous findings have demonstrated an increased susceptibility of tumors to NK cell-mediated lysis. However, it appears that the triggering mechanism of CD80 on NK cells is independent of its typical ligands, such as CD28 and CTLA-4. CD80 has not yet been explored as a target for engineering in feeder cells used for the expansion of NK cells; therefore, it can be exploited as a new stimulator for the in vitro expansion of NK cells.

As per Patent No. US20210230548A1, the patent covers techniques for generating NK cells that express chimeric antigen receptors. This involves modifying isolated natural killer (NK) cells to express (1) a chimeric antigen receptor (CAR) and/or a T cell receptor (TCR), and (2) human IL-15 (hIL-15) while having no expression of CISH.

As per Patent No. CN113383069A, the invention involves a method for culturing cord blood-derived natural killer cells utilizing transformed T cells. In this method, the transformed CD4+ T cells express at least one gene selected from the group consisting of 4-1BBL, mbIL-21, OX40L, and mTNF-α genes.

As per Patent No. CN113383069A, the invention refers to a cell membrane expressing 4-1BBL and IL-15 on its surface. The method for preparing this cell membrane involves:

(1) preparing expression plasmids for IL-15 and 4-1BBL proteins;

(2) transfecting cells with the expression plasmids for IL-15 and 4-1BBL proteins;

(3) collecting and crushing cells that successfully express the target proteins to prepare fragments of cell membranes;

(4) the cell membrane is derived from K562 cells.

The aforementioned inventions fulfill specific purposes and meet the requirements of a technical solution. However, the disclosed invention does not involve utilizing CD80 as a stimulator for expanding cord-blood NK cells from different donors by expressing the gene, both alone and in combination with 4-1BBL and membrane-bound IL-21 (mbIL-21), within the K562 cell line. Rather than solely comparing a single targeted stimulatory factor to wild-type K562 cells, our approach involved simultaneous investigation of CD80 stimulation on NK cells alongside 4-1BBL and mbIL-21. Each stimulator was individually expressed in the K562 cell line, followed by a subset undergoing secondary and, in some cases, tertiary transduction to create 2-factor or 3-factor stimulatory K562-based feeder cells. Additionally, we explored the feeder-free expansion of NK cells using IL-2 and IL-15 cytokines, offering an overview of current strategies for in vitro culture of NK cells. Furthermore, our exploration included the transduction of a chimeric antigen receptor (CAR) construct into expanding NK cells using various lentiviral vectors, and the functionality of these cells post-transduction.

Therefore, it is necessary to modify K562 cells capable of increasing the activation and proliferation of NK cells isolated from cord blood.

Finally, it is necessary to generate or expand a population of NK cells by culturing the NK cells isolated from cord blood in the presence of a modified K562 cell for 14 days.

The invention provides solutions to achieve the above objectives.

SUMMARY OF THE INVENTION

Accordingly, a primary aspect of the present invention is to provide modified K562 feeder cells that express factors capable of enhancing the activation and proliferation of natural killer cells. These factors include: (A) a co-stimulatory molecule selected from the group consisting of CD80, 4-1BBL, and combinations thereof; and (B) a cytokine, specifically membrane-bound IL-21 (mbIL-21).

A second aspect of the present invention is to provide a method for producing modified K562 feeder cells expressing factors capable of increasing the activation and proliferation of natural killer cells. This method comprises two stages: (A') a first stage involving the preparation of materials, including a K562 cell suspension, and a medium containing a lentiviral vector carrying a co-stimulatory molecule and cytokine; and (B') a second stage involving K562 transduction.

A third aspect of the present invention is to provide a method for generating or expanding a population of natural killer cells (NK cells) comprising:

(i) isolating and purifying NK cells from a cord blood sample using a gradient centrifugation method;

(ii) preparing modified K562 feeder cells expressing factors capable of increasing the activation and proliferation of natural killer cells; and (iii) expanding a population of NK cells by culturing the NK cells isolated at step (i) in the presence of the modified K562 cell at step (ii) for 14 days.

Yet another objective of the present invention is to provide a pharmaceutical composition comprising a population of NK cells produced by the method according to the third aspect, and a pharmaceutically acceptable carrier.

In view of the foregoing, another objective of the present invention is to provide a composition comprising a population of NK cells produced by the method according to the third aspect for use in the treatment of a disease, cancer, or disorder in a subject.

Finally, the purpose of the invention is to provide a method of treating or preventing a disease or cancer or disorder through administering a population of NK cells produced by the method according to the third aspect in a subject.

These and other advantages of the present invention will undoubtedly become apparent to those of ordinary skill in the art after reading the following detailed description of the preferred embodiments, illustrated in the various drawing figures.

BRIEF DESCRIPTION OF THE DRAWING

The accompanying drawings, which are incorporated in and form a part of this specification, illustrate embodiments of the invention and, together with the description, serve to explain the principles of the invention.

FIG. 2A is an image illustrating the plasmid map of the vector carrying the co-stimulatory molecule 4-1BBL according to an embodiment of the present invention;

FIG. 2B is an image illustrating the plasmid map of the vector carrying the CD80 molecules according to an embodiment of the present invention;

FIG. 3A is an image illustrating the expression of CD80 molecules in the modified K562 feeder cells according to an embodiment of the present invention;

FIG. 3B is an image illustrating the expression of 41BBL molecules in the modified K562 feeder cells according to an embodiment of the present invention;

FIG. 3C is an image illustrating the expression of mbIL-21 molecules in the modified K562 feeder cells according to an embodiment of the present invention;

FIG. 3D is an image illustrating the expression of co-expressing 41BBL molecules and mbIL21 molecules in the modified K562 feeder cells according to an embodiment of the present invention;

FIG. 3E is an image illustrating the expression of co-expressing CD80 molecules and mbIL21 molecules in the modified K562 feeder cells according to an embodiment of the present invention;

FIG. 3F is an image illustrating the expression of co-expressing CD80 molecules and 41BBL molecules in the modified K562 feeder cells according to an embodiment of the present invention;

FIG. 3G is an image illustrating the expression of co-expressing CD80 molecules, 41BBL molecules, and mbIL21 molecules in the modified K562 feeder cells according to an embodiment of the present invention;

DETAILED DESCRIPTION OF THE INVENTION

Figure 1:
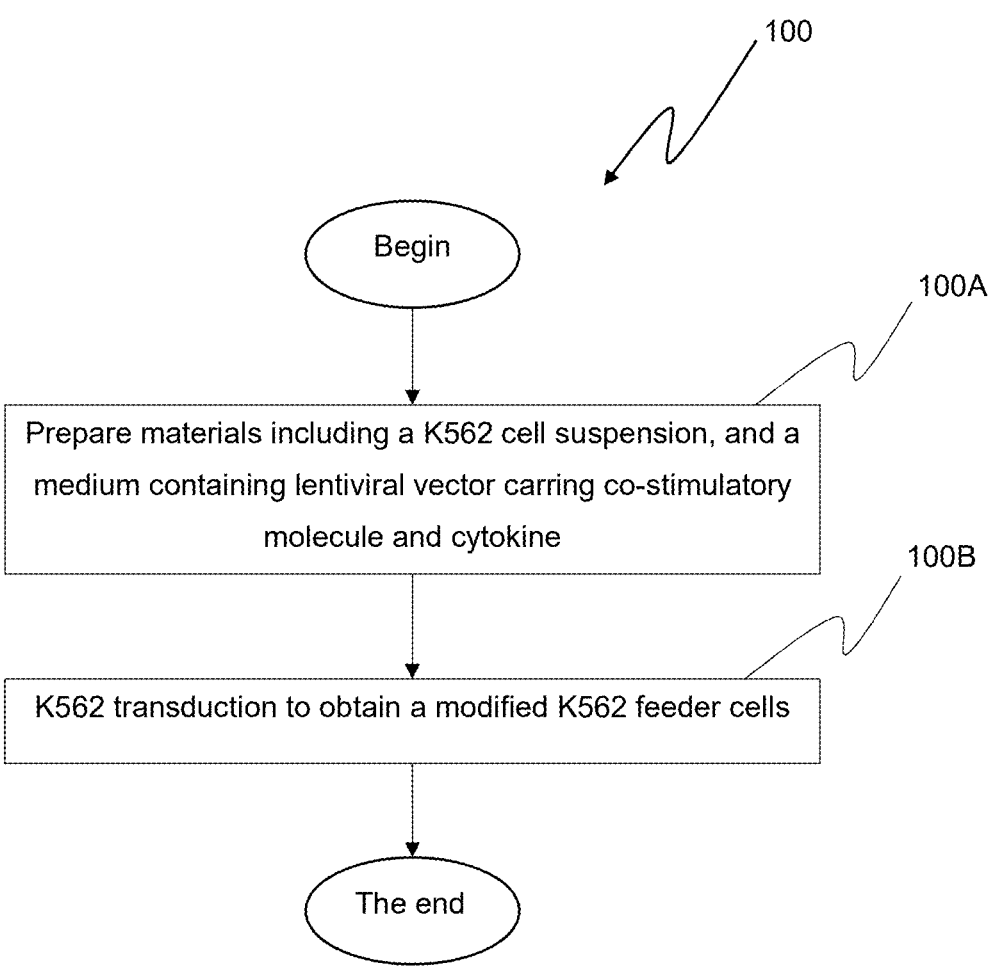
FIG. 1 is a flowchart illustrating a method for producing the modified K562 feeder cells having the expression of factors capable of increasing the activation and proliferation of natural killer cells according to an embodiment of the present invention.

Reference will now be made in detail to the preferred embodiments of the invention, examples of which are illustrated in the accompanying drawings. While the invention will be described in conjunction with these preferred embodiments, it should be understood that they are not intended to limit the invention. On the contrary, the invention is intended to cover alternatives, modifications, and equivalents that may be included within the spirit and scope of the invention as defined by the appended claims. Furthermore, in the following detailed description of the present invention, numerous specific details are set forth to provide a thorough understanding. However, it will be obvious to one of ordinary skills in the art that the present invention may be practiced without these specific details. In other instances, well-known methods, procedures, components, and circuits have not been described in detail so as not to unnecessarily obscure aspects of the present invention.

It should be noted that the terms "first", "second" and the like in the specification and claims of the present invention are used to distinguish similar objects and are not necessarily indicative of a specific order. It is to be understood that the terms are interchangeable, where appropriate, allowing the embodiments of the invention described herein to be implemented in a sequence other than those illustrated or described. Additionally, the terms "comprises" and "comprising", as well as "the" and "these", are intended to cover a non-exclusive inclusion. For example, a process, method, system, product, or device that comprises a series of steps or units is not necessarily limited to those explicitly listed and may include other steps or units not explicitly mentioned or inherent to such processes, methods, products, or devices.

It should be noted that the term "room temperature" or "RT" of the present invention refers to a temperature condition 20° C. to 22° C.

The term "natural killer" or "NK" refers to cells that are cytotoxic lymphocytes that constitute a significant component of the innate immune system.

The headings provided herein are not intended to limit the disclosure.

In the following, to facilitate the understanding of the present solution, some proper nouns appearing in the subsequent embodiments of the present application are explained.

An "immune disorder", "immune-related disorder", or "immune-mediated disorder" refers to a condition in which the immune response plays a key role in the development or progression of the disease. Immune-mediated disorders include autoimmune disorders, allograft rejection, graft-versus-host disease, and inflammatory and allergic conditions.

"Treating" or treatment of a disease or condition refers to executing a protocol, which may include administering one or more drugs to a patient, in an effort to alleviate signs or symptoms of the disease. Desirable effects of treatment include decreasing the rate of disease progression, ameliorating or palliating the disease state, and achieving remission or an improved prognosis. Alleviation can occur before signs or symptoms of the disease or condition appear, as well as after their appearance. Thus, "treating" or "treatment" may include "preventing" or "prevention" of the disease or undesirable condition. In addition, "treating" or "treatment" does not require complete alleviation of signs or symptoms, does not necessitate a cure, and specifically includes protocols that have only a marginal effect on the patient.

"Subject" and "patient" refer to either a human or non-human, such as primates, mammals, and vertebrates. In particular embodiments, the subject is a human.

The phrases "pharmaceutical or pharmacologically acceptable" refer to molecular entities and compositions that do not produce an adverse, allergic, or other untoward reaction when administered to an animal, such as a human, as appropriate. The preparation of a pharmaceutical composition comprising an antibody or an additional active ingredient will be known to those of skill in the art in light of the present disclosure. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all aqueous solvents (e.g., water, alcoholic/aqueous solutions, saline solutions, parenteral vehicles such as sodium chloride, Ringer's dextrose, etc.), non-aqueous solvents (e.g., propylene glycol, polyethylene glycol, vegetable oil, and injectable organic esters such as ethyloleate), dispersion media, coatings, surfactants, antioxidants, preservatives (e.g., antibacterial or antifungal agents, antioxidants, chelating agents, and inert gases), isotonic agents, absorption-delaying agents, salts, drugs, drug stabilizers, gels, binders, excipients, disintegration agents, lubricants, sweetening agents, flavoring agents, dyes, fluid and nutrient replenishers, and similar materials and combinations thereof, as would be known to one of ordinary skill in the art. The pH and exact concentration of the various components in a pharmaceutical composition are adjusted according to well-known parameters.

The first aspect of the present invention is to provide a method for producing the modified K562 feeder cells expressing factors capable of increasing the activation and proliferation of natural killer cells 100 ("method 100") comprises two stages: a first stage 100A preparing materials including a K562 cell suspension, and a medium containing lentiviral vector carrying co-stimulatory molecule and cytokine; and a second stage 100B performing K562 transduction.

According to the embodiment of the invention, stage 100A, prepare the K562 cell suspension by expanding K562 cells in roswell park memorial institute (RPMI) 1640 supplemented 10% heat-inactivated fetal bovine serum (FBS), and 1% penicillin-streptomycin at maximum $10^6$ cells/ml at 37° C. under 5% $CO_2$ for 7 days, and irradiated with 100 Gy.

According to the embodiment of the invention, stage 100A, prepare the medium containing lentiviral vector carrying co-stimulatory molecule and cytokine by performed in the following (a)-(e):

(a) preparing a 293T cell line by expanding 293T cells from a passage 7 or 8 in a 10-cm dish until the confluency reaches 80-90%, then change medium to serum-reduced 1 hour before performing at step (b);

(b) preparing a plasmid mixture by performed in the following:

(b1) preparing 1.5 mL of tube A by mixing 900 μl said medium serum-reduced with 2.8 μg RSV/Rev with 3.5 μg MD2G/VSV, 5.7 μg MDLg/RRE, and 14 μg transgene plasmid; wherein the transgene plasmid includes the co-stimulatory molecule and the cytokine;

the co-stimulatory molecule is selected from the group consisting of CD80, 4-1BBL, and combinations thereof; and the cytokine is membrane-bound IL-21 (mbIL-21);

(b2) preparing 2 mL of tube B obtained by mixing 900 μl the medium at step (a) with 52 μl of transfection reagent;

(b3) incubating the tube B at RT for 4 min; and (b4) admixing the solution of tube A at step (b1) into the incubated solution of tube B at step (b3), then incubated at room temperature for 30 min to obtain the plasmid mixture;

(c) transfecting the plasmid mixture into the 293T cell line at step (a), followed by incubation at 37° C. for 6 hours;

(d) replacing the medium with DMEM 10% FBS (approximately 7-8 ml/dish) at 6 hours post-transfection, then incubating at 37° C.; and (e) collecting viral supernatant at 48 hours post-transfection; wherein the viral supernatant is the medium containing the lentiviral vector carrying the co-stimulatory molecule and the cytokine.

According to the embodiment of the invention, the plasmid map of the vector carrying the co-stimulatory molecule 4-1BBL is referenced in FIG. 2A, wherein the 4-1BBL molecule refers to a polypeptide with the sequence of SEQ ID NO: 1.

According to the embodiment of the invention, the plasmid map of vectors carrying CD80 molecules is referenced by FIG. 2B, wherein the CD80 molecule refers to a polypeptide with the sequence of SEQ ID NO: 2.

Figure 2C:
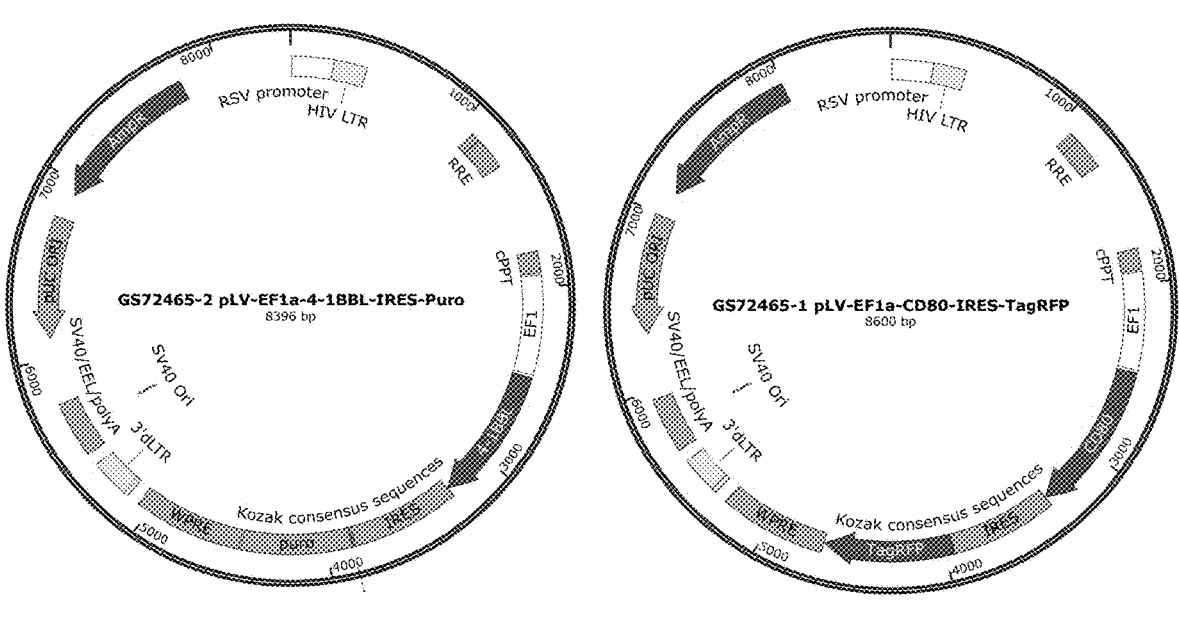
FIG. 2C is an image illustrating the plasmid map of the vector carrying mbIL-21 according to an embodiment of the present invention.
Figure 2C:
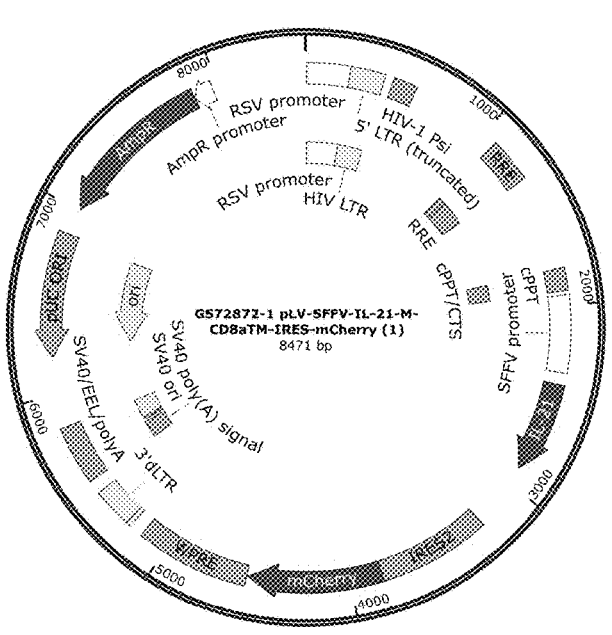

According to the embodiment of the invention, the plasmid map of vectors carrying mbIL-21 is referenced by FIG. 2C, wherein the mbIL-21 molecule refers to a polypeptide with the sequence of SEQ ID NO: 3.

At stage 100B, performing K562 transduction comprising steps (a') to (g'):

(a') mixing 10 μl of K562 cell suspension at first stage (A') with 10 μl of trypan blue, then counting K562 cells with trypan blue;

(b') transferring $2\times10^5$ cells for transduction of each gene into two tubes, including $10^5$ cells for control tube, and $10^5$ cells for transduction tube;

(c') washing cells with PBS, then centrifuging at 200×g for 4 minutes to obtain a resuspended cells;

(d') admixing the resuspended cells into two tubes:

admixing the resuspended cells into a control tube with 500 μl RPMI 10% FBS and transferring to a 24-well plate;

admixing the resuspended cells into a transduction tube with 500 μl of viral supernatant and transferring to another 24-well plate;

(e') admixing 4 μg of polybrene in each well, then sealing the plate with parafilm, and centrifuging the plate at 33° C. with speed at 1000×g for 90 minutes;

(f') incubating the centrifuged plates overnight, then change the medium includes 500 μl of fresh RPMI, 10% FBS, and 1% Pen-Strep, and culturing for 7 days; and (g') collecting single cell clones expressing co-stimulatory molecules and cytokines as the modified K562 feeder cells through assessed transgene expression at day 7 by flow cytometry.

In the embodiment of the present invention, the modified K562 feeder cells obtained by method 100 which express a single molecule is selected from the group consisting of CD80, 41BBL, and mbIL-21; including:

the expression of CD80 molecules in the modified K562 feeder cells as shown in FIG. 3A;

the expression of 41BBL molecules in the modified K562 feeder cells as shown in FIG. 3B; and the expression of mbIL-21 molecules in the modified K562 feeder cells as shown in FIG. 3C.

In the embodiment of the present invention, the modified K562 feeder cells obtained by method 100 which co-expressing two molecules is selected from the group consisting of 41BBL-mbIL21, CD80-mbIL21, and CD80-41BBL; including:

the expression of co-expressing 41BBL molecules and mbIL21 molecules in the modified K562 feeder cells as shown in FIG. 3D;

the expression of co-expressing CD80 molecules and mbIL21 molecules in the modified K562 feeder cells as shown in FIG. 3E; and the expression of co-expressing CD80 molecules and 41BBL molecules in the modified K562 feeder cells as shown in FIG. 3F.

In the embodiment of the present invention, the modified K562 feeder cells obtained by method 100 which co-expressing CD80, 41BBL, and mbIL-21, as shown in FIG. 3G.

The second aspect of the present invention is to provide a modified K562 feeder cell having expression of factors capable of increasing the activation and proliferation of NK cells, in which the factors capable of increasing activation and proliferation of natural killer cells comprising: (A) a co-stimulatory molecule includes CD80, and 4-1BBL; and (B) a cytokine is membrane-bound IL-21 (mbIL-21).

Figure 4:
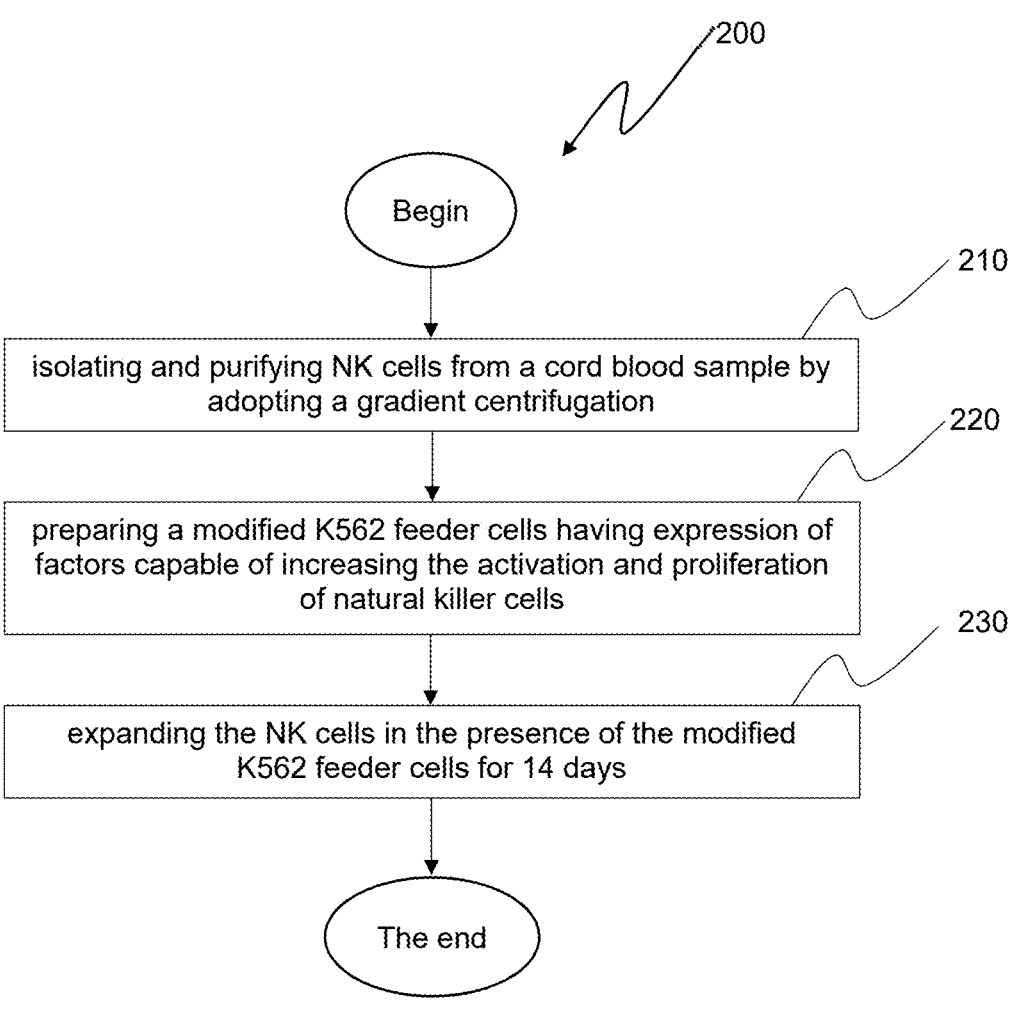
FIG. 4 is a flowchart illustrating a method for generating or expanding a population of natural killer (NK) cells according to an embodiment of the present invention.

The third aspect of the present invention is to provide a method for generating or expanding the population of natural killer cells (NK cells) 200 ("method 200") in accordance with an exemplary embodiment of the present invention. Refer to FIG. 4, method 200 includes the following steps:

At step 210, isolating and purifying NK cells from a cord blood sample is performed by adopting a gradient centrifugation method. In the embodiment of the invention, isolating NK cells from the cord blood sample is performed as follows:

(a1) collecting the cord blood sample in a bag, then preserve it in a polystyrene box with a gel ice pack;

(a2) preparing 6-8 50-ml tubes pre-filled with 30 ml of PBS, depending on the volume of the collected cord blood sample;

(a3) cleaning the blood bag with 70% ethanol before bringing it into the cabinet, and sterilize scissors with 70% ethanol;

(a4) checking the tubing of the blood bag, ensuring the valve is right below the cut point and is closed;

(a5) mixing the blood by gently tilting the blood bag; cut the tubing and open the valve to allow the blood to flow into the prepared PBS tubes. For each tube, the diluted blood level reaches about 45-50 mL (2-fold dilution);

(a6) preparing Lymphoprep (avoiding light) in 50-ml tubes; 15 ml Lymphoprep/tube. Calculate the total number of tubes needed by dividing the total volume of diluted blood by 30;

(a7) loading diluted blood on Lymphoprep: incline the Lymphoprep tube and gently expel blood with a pipette gun at the top of the tube, allow the blood to flow down onto the Lymphoprep layer;

(a8) loading 30 ml of diluted blood into each Lymphoprep tube;

(a9) centrifuging at 1000×g for 30 minutes, with acceleration and deceleration speed turned off (=0, press twice on the time button to set acceleration speed and brake), maintain a temperature of 20° C.-24° C.;

(a10) collecting the whitish ring separating plasma from Lymphoprep into a 50-ml tube;

(a11) washing the collected cell suspension by adding 20-30 ml of PBS/tube, distribute the cell suspension 20-30 ml/tube, and adding PBS to obtain a full 50 ml of suspension;

(a12) centrifuging at 300×g for 10 minutes;

(a13) cord blood PBMCs are usually heavily contaminated with red blood cells; if the pellet collected is all red, perform a lysis with RBC Lysis buffer: add 5 mV/tube, incubate on ice or in the fridge for 5 minutes, then stop the lysis by adding 30 ml PBS;

(a14) centrifuging at 250×g for 5 minutes, turning off acceleration and deceleration to eliminate RBC Lysis buffer and platelets, to obtain a cell pellet after washing having a white appearance;

(a15) counting PBMCs by performing in following steps: resuspending pellets from all tubes in 30 ml, to a second 50-ml tube, adding 25 ml of PBS, taking 5 ml from the cell suspension to add to the PBS tube, creating a 6-fold dilution, counting cells with 10 μl from the diluted tube, admixing 10 μl of trypan blue, and calculating the total cell number by density inferred from trypan blue cell count×30 ml×6; and (a16) isolating NK cells by performing in following steps: adding $5\times10^7$-$10^8$ cells into a new tube, then adding PBS to wash cells; wherein storing $5\times10^6$-$10^7$ cells/ml/cryotube for the remaining PBMCs with FBS supplemented 10% DMSO, or culturing the remaining PBMCs with 50 ng/ml anti-CD3 in a serum-free lymphocyte medium such as AIM-V™ medium supplemented with 10% FBS to enrich T cells.

According to the embodiment of the invention, NK cell purification is performed by referring to the protocol from the MojoSort Human NK Cell Isolation Kit, as follows:

(a1') counting $1\times10^8$ PBMCs, and resuspending washed cells in 1 ml of Mojo buffer;

(a2') adding 100 μl of the antibody cocktail, then incubating on ice for 15 minutes;

(a3') adding 3 ml of Mojo buffer, then centrifuging at 300×g for 5 minutes, and discard the supernatant;

(a4') resuspending the cell pellet in 1 ml of Mojo buffer, then adding 100 μl of Mojo beads, and incubating for 15 minutes on ice;

(a5') adding 3 ml of Mojo buffer, then centrifuging at 300×g for 5 minutes, and removing the supernatant;

(a6') resuspending the cell pellet in 2.5 ml of Mojo buffer and transfer the cell suspension to a sterile 5-ml tube (FACS tube with cap, preserved in the enclosed package);

(a7') mixing well before putting the tube into the yellow magnet from Biolegend, then leaving the tube on the magnet for 5 minutes;

(a8') pouring out the supernatant into a sterile 15-ml tube; repeating the magnetic sorting step by adding 1-2 ml of Mojo buffer, mixing well, then placing the tube into the magnet for 5 minutes; and (a9') pouring out the supernatant into the same collection tube, and mixing gently, then counting cells with trypan blue: 10 μl of cell suspension and 10 μl of Trypan Blue.

Still with FIG. 4, at step 220, prepare the modified K562 feeder cells expressing factors capable of enhancing the activation and proliferation of natural killer cells, in which the factors capable of increasing activation and proliferation of natural killer cells comprising: (A) a co-stimulatory molecule includes CD80, and 4-1BBL; and (B) a cytokine is membrane-bound IL-21 (mbIL-21).

According to the preferred embodiment of the invention, the modified K562 feeder cells co-expressing CD80, 41BBL, and mbIL-21 which are prepared according to the method 100 has been described in detail above.

Finally, at step 230, generating or expanding a population of NK cells by culturing the NK cells isolated at step 210 in the presence of the modified K562 feeder cells at step 220 for 14 days, comprising following in steps:

At day 0, co-culturing the NK cells at step 210 in vitro or ex vivo in the presence of the modified K562 feeder cells at step 120 at a ratio of the modified K562 feeder cells to the NK cells of 5:1 in AIM-V™ medium supplemented with 10% FBS, and 200 IU/ml IL-2;

At day 7, counting the number of NK cells, then adding the modified K562 feeder cells to fresh AIM-V™ medium supplemented with 10% FBS, and 200 IU/ml IL-2; wherein a ratio between counted the number of the modified K562 cell and the NK cells is 5:1, in which the modified K562 feeder cells are treated with irradiation at 100 Gy;

At day 7, performing CAR-lentivirus transduction into NK cells, comprising following in steps:

precoating disks overnight at 4° C. with the reagent enhances lentivirus-mediated gene delivery at 5 μg/cm², in which the reagent enhances lentivirus-mediated gene delivery is a fibronectin-derived viral transduction reagent such as RetroNectin®;

preparing the lentiviral supernatant containing the viral vector encoding the CAR, then introducing into the 24-well plates and centrifuged at 2000 g for 1.5 hours at 4° C.;

adding NK cells into the centrifuged 24-well plates containing lentiviral supernatant and centrifuged the co-cultured mixture at 1000×g for 1 hour at 32° C.; and culturing post-transduction cells in fresh AIM-V™ medium supplemented with 10% FBS, and 200 IU/ml IL-2;

At day 8, replacing the culture medium with fresh AIM-V™ medium supplemented 10% FBS, and 200 IU/ml IL-2.

At day 10, counting the number of NK cells, then adding the modified K562 feeder cells to fresh AIM-V™ medium supplemented with 10% FBS, and 200 IU/ml IL-2; wherein a ratio between counted the number of NK cells and the modified K562 cell is 1:1, in which the modified K562 feeder cells are treated with irradiation at 100 Gy; and Finally, at day 14, collect the population of NK cells that are competent with high cytotoxicity.

Referring to the results, the expression of co-stimulatory molecules and mbIL-21 in the modified K562 feeder cells (abbreviated as feeder cells) is examined.

(B1) Material: The K562 cell line was procured from the American Type Culture Collection (ATCC). Modified K562 feeder cell lines expressing CD80, 4-1BBL, or membrane-bound IL-21, either individually or in combination, were generated by transducing K562 cells with CD80-, 4-1BBL-, or mbIL-21-lentivirus and subsequently sorted using the WOLFG2 Cell Sorter. These cells and their derivatives were cultured in RPMI 1640 (Gibco, USA) supplemented with 10% heat-inactivated fetal bovine serum (FBS) and 1% penicillin-streptomycin at 37° C. under 5% CO₂. The 293T cell line was purchased from Takara Bio (USA) and maintained in DMEM (Gibco, USA) supplemented with 10% FBS and 1% penicillin-streptomycin. Gastric cancer cell line MKN-45 cells were generously provided by Dr. Phu-Hung Nguyen (Thai Nguyen University of Science, Thai Nguyen, Viet Nam) and cultured in RPMI 1640 medium supplemented with 10% FBS and 1% penicillin-streptomycin. Additionally, MCF-7 cells were kindly provided by Dr. Thuy-Vy Nguyen (Ho Chi Minh City University of Science, Ho Chi Minh City, Viet Nam) and maintained in DMEM (Gibco, USA) medium supplemented with 10% FBS and 1% penicillin-streptomycin. Before experimentation, all cell lines were rigorously tested and confirmed negative for *mycoplasma* contamination.

Figure 5:
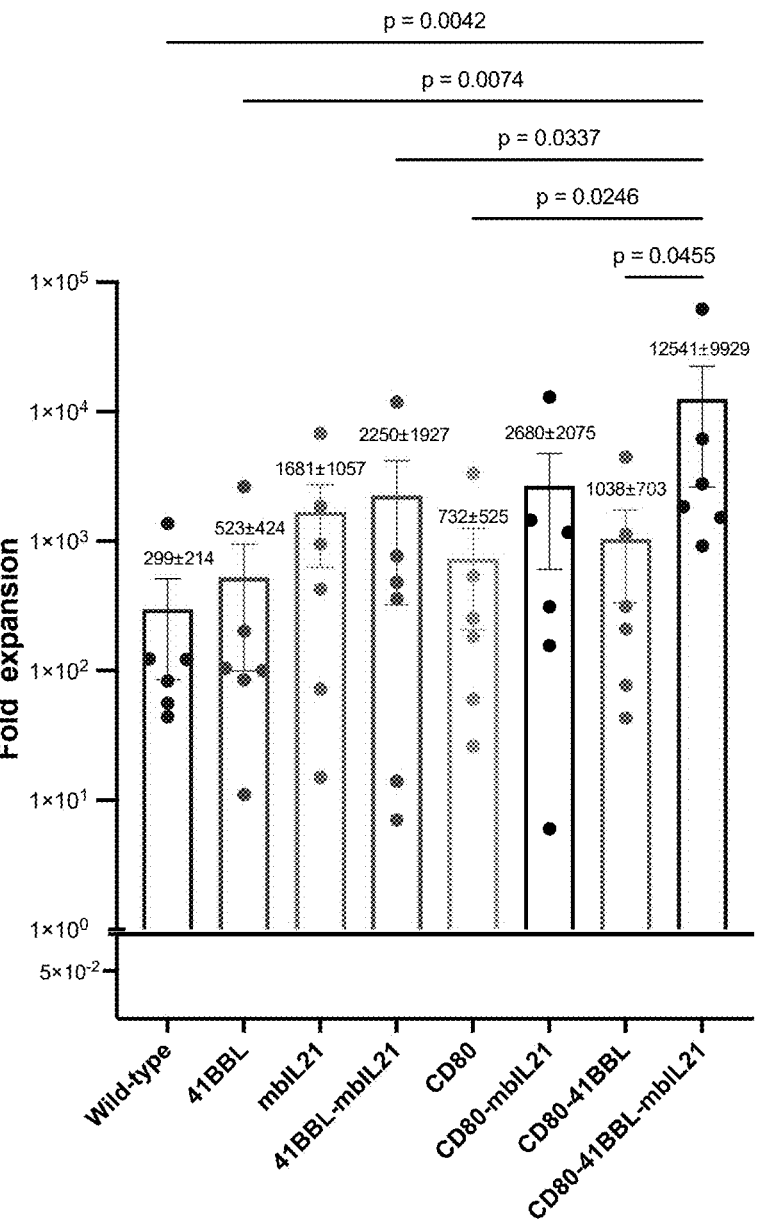
FIG. 5 is an image illustrating the fold expansions of NK cells cultured with the modified K562 feeder cells co-expressing CD80, 41BBL, and mbIL-21 with the NK cells cultured without modified K562 feeder cells (feeder-free), or with different the modified K562 feeder cells irradiated, including wild-type, 41BBL, mbIL21, 41BBL-mbIL21, CD80, CD80-mbIL21, and CD80-41BBL.

(B2) Results: the modified K562 feeder cells co-expressing CD80, 41BBL, and mbIL-21 achieves better efficiency compared to the modified K562 feeder cells expressing the single molecule and the modified K562 feeder cells co-expressing two molecules. This is demonstrated based on the evaluation criteria results, including:

(a) Comparing fold expansions of NK cells cultured with the modified K562 feeder cells co-expressing CD80, 41BBL, and mbIL-21 with NK cells cultured without modified K562 feeder cells (feeder-free), or with different the modified K562 feeder cells irradiated, including wild-type, 41BBL, mbIL21, 41BBL-mbIL21, CD80, CD80-mbIL21, and CD80-41BBL. The result showed that NK cells cultured with the modified K562 feeder cells showed higher levels of expansion compared to the feeder-free approach, although there was no significant difference detected as shown in FIG. 5.

Figure 6:
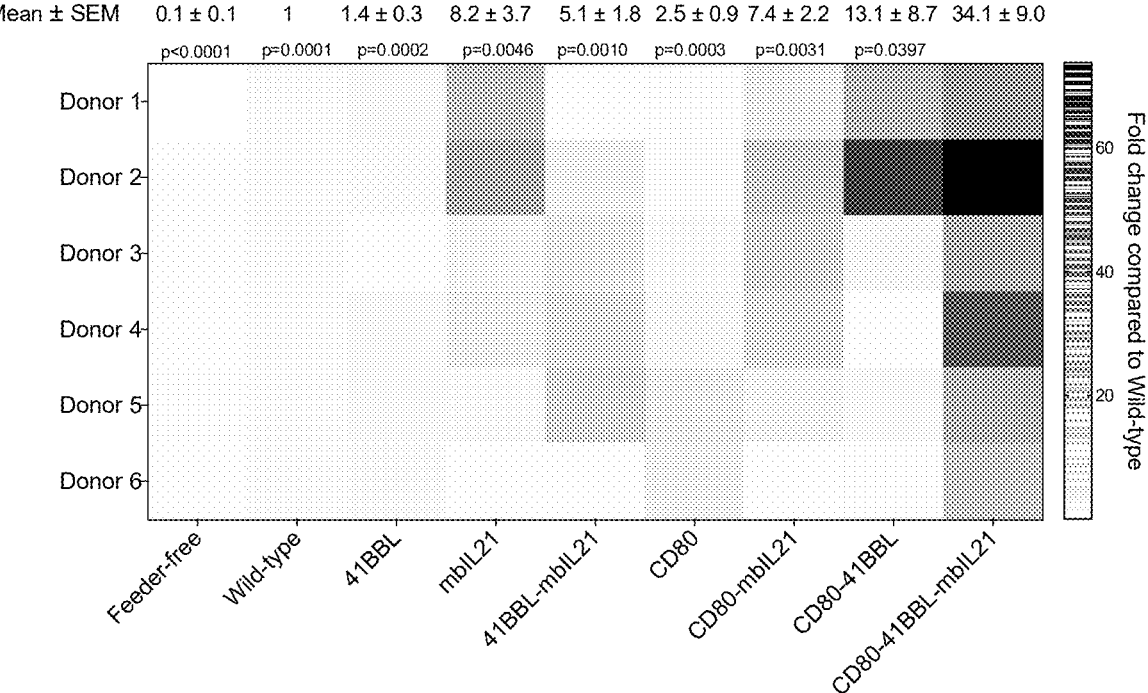
FIG. 6 is an image illustrating the expansion rates of NK cells cultured with the modified K562 feeder cells co-expressing CD80, 41BBL, and mbIL-21 with NK cells cultured without modified K562 feeder cells (feeder-free), or with different the modified K562 feeder cells irradiated, including wild-type, 41BBL, mbIL21, 41BBL-mbIL21, CD80, CD80-mbIL21, and CD80-41BBL.

(b) Comparing expansion rates of NK cells cultured with the modified K562 feeder cells co-expressing CD80, 41BBL, and mbIL-21 with NK cells cultured without modified K562 feeder cells (feeder-free), or with different the modified K562 feeder cells irradiated, including wild-type, 41BBL, mbIL21, 41BBL-mbIL21, CD80, CD80-mbIL21, and CD80-41BBL. The result showed that NK cells cultured with CD80-41BBL-mbIL21 K562 consistently demonstrated the highest expansion rates across all six donors (as shown in FIG. 5). When comparing fold expansions normalized to NK cells cultured with Wild-type K562 cells, NK cells cultured with CD80-41BBL-mbIL21 K562 exhibited the highest fold change among the seven tested feeder cells (as shown in FIG. 6). Notably, NK cells exhibited significantly higher expansion rates when cultured with CD80-41BBL-mbIL21 compared to the conventional 41BBL-mbIL21 K562 cells, which are currently used by many research groups (34.4±9 versus 5.1±1.8, p=0.0003). These data suggest that the co-expression of the co-stimulatory molecules CD80 in the conventional 41BBL-mbIL21 feeder cells significantly enhances NK cell expansion across different donors.

Figure 7:
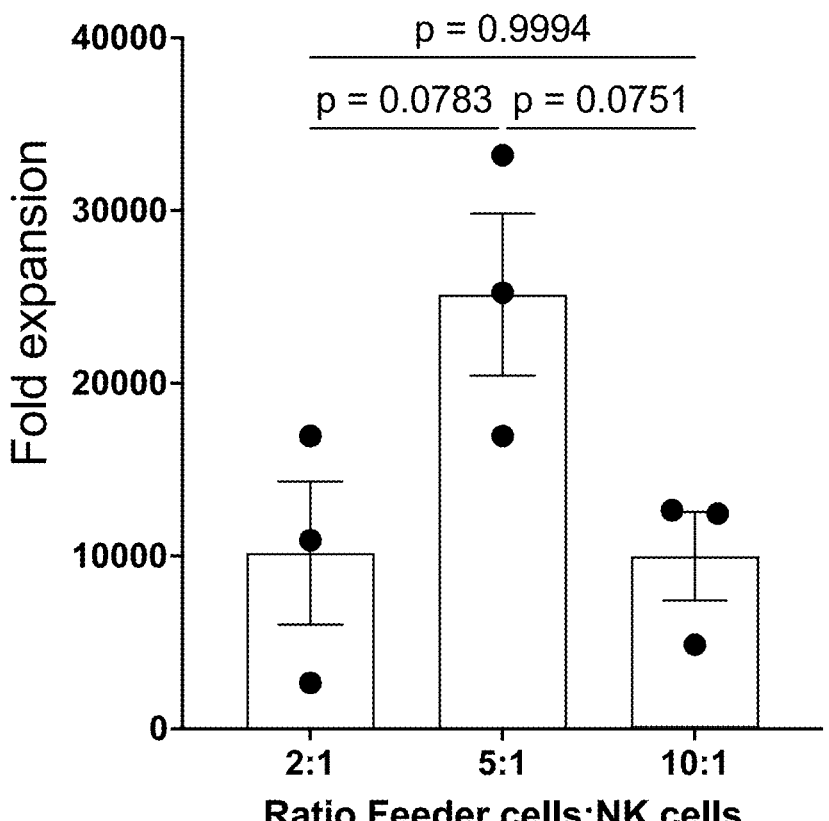
FIG. 7 is an image illustrating the NK cells fold expansion surveyed different ratios between the modified K562 feeder cells co-expressing CD80, 41BBL, and mbIL-21 and the NK cells in the culture medium included 2:1, 5:1, and 10:1.
Figure 8:
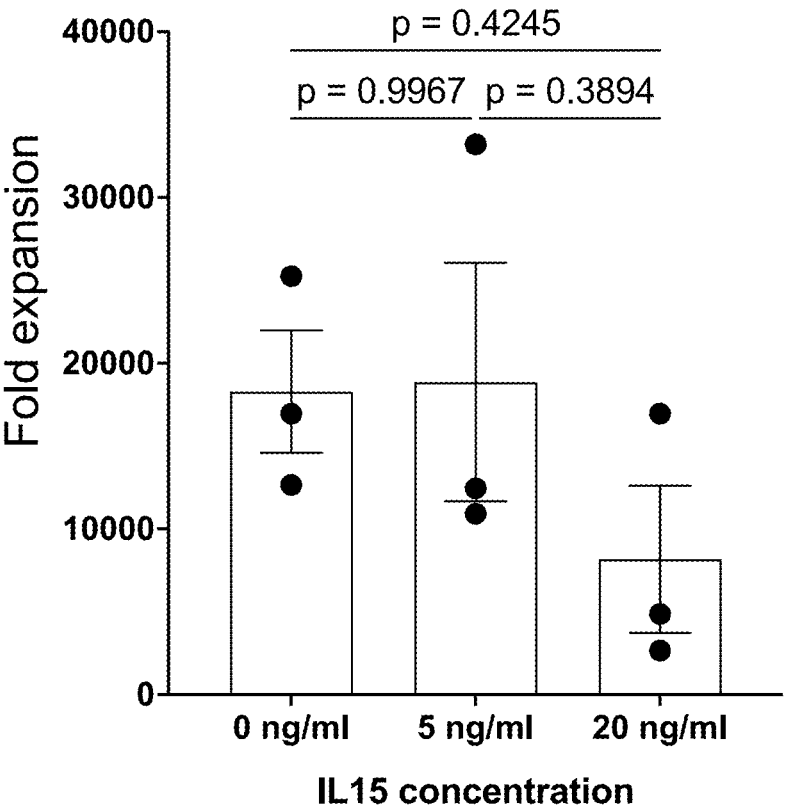
FIG. 8 is an image illustrating the NK cells fold expansion surveyed different IL15 concentrations including 0 ng/ml, 5 ng/ml, and 20 ng/ml in the culture medium having a ratio between the modified K562 feeder cells co-expressing CD80, 41BBL, and mbIL-21 and the NK cells is 5:1.

Optimizing the technical parameters at step 230 of the method 200 to offer the highest NK cell expansion, including:

(a') Surveying different ratios between the modified K562 feeder cells co-expressing CD80, 41BBL, and mbIL-21 and the NK cells in the culture medium included 2:1, 5:1, and 10:1. The result showed that the ratio 5:1 tends to have higher fold expansion than the ratio 2:1 and 10:1 (as shown in FIG. 7); and (b') Surveying different IL15 concentrations including 0 ng/ml, 5 ng/ml, and 20 ng/ml in the culture medium having a ratio between the modified K562 feeder cells co-expressing CD80, 41BBL, and mbIL-21 and the NK cells is 5:1. The result showed that without IL15, NK cells still could grow equally to the group containing IL15 (as shown in FIG. 8). It indicated that the modified K562 feeder cells co-expressing CD80, 41BBL, and mbIL-21 can support NK cells growing without IL15.

Figure 9:
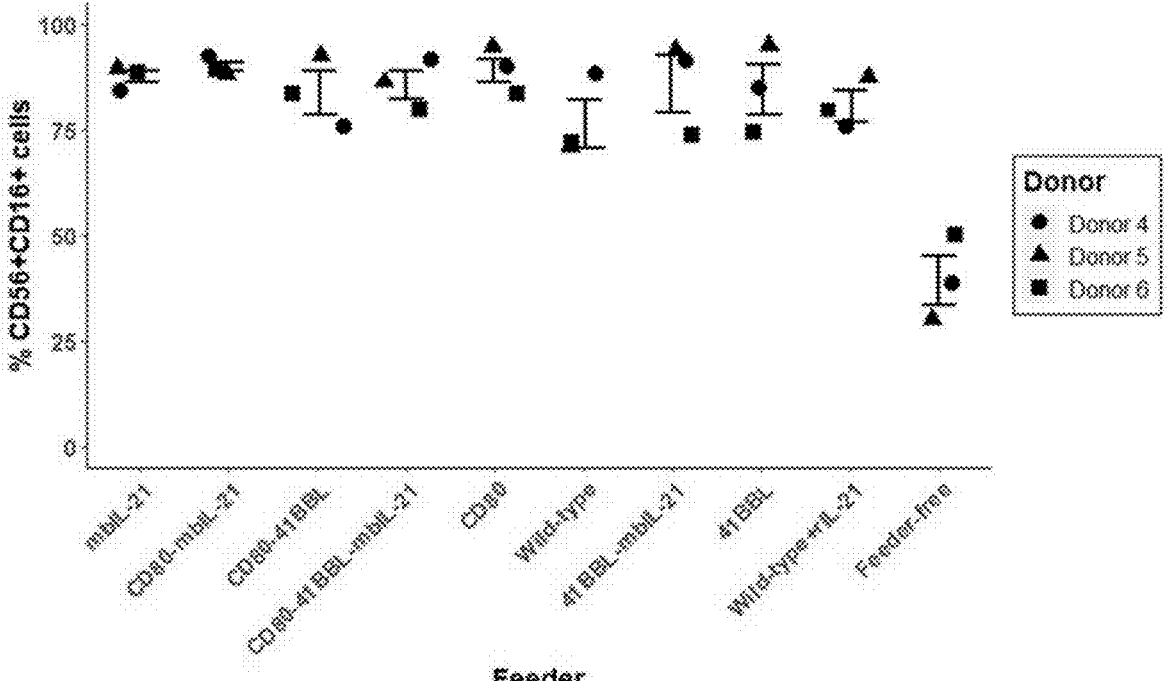
FIG. 9 is a graph illustrating a comparison between the phenotypes of NK cells expanded with the modified K562 feeder cells and the feeder-free approach according to an embodiment of the present invention.

Referring to FIG. 9, the results compare the phenotype of NK cells expanded with the modified K562 feeder cells and the feeder-free method. The phenotype analysis is based on the expression of CD56 and CD16. CD56 serves as a marker for NK cells, while CD16 expression may vary among different subsets of NK cells, with high CD16 expression indicating a mature phenotype with enhanced cytotoxic capacity and potential killing activity through antibody-dependent cellular cytotoxicity. NK cells expanded from co-culture with both wild-type and modified K562 feeder cells that exhibited a high co-expression of CD56 and CD16. Whether with engineered or wild-type feeder cells, the proportion of CD16+ in the CD56+ population consistently exceeded 80%. In contrast, the feeder-free method provided only 30.2%-50.1% of CD56+ cells with CD16 expression. This indicates that the feeder-dependent method, whether using wild-type or modified K562 feeder cells, was more efficient than the feeder-free method in inducing a mature phenotype of expanded NK cells.

Figures 10A, 10B, 10C, 10D, 10E, 10F:
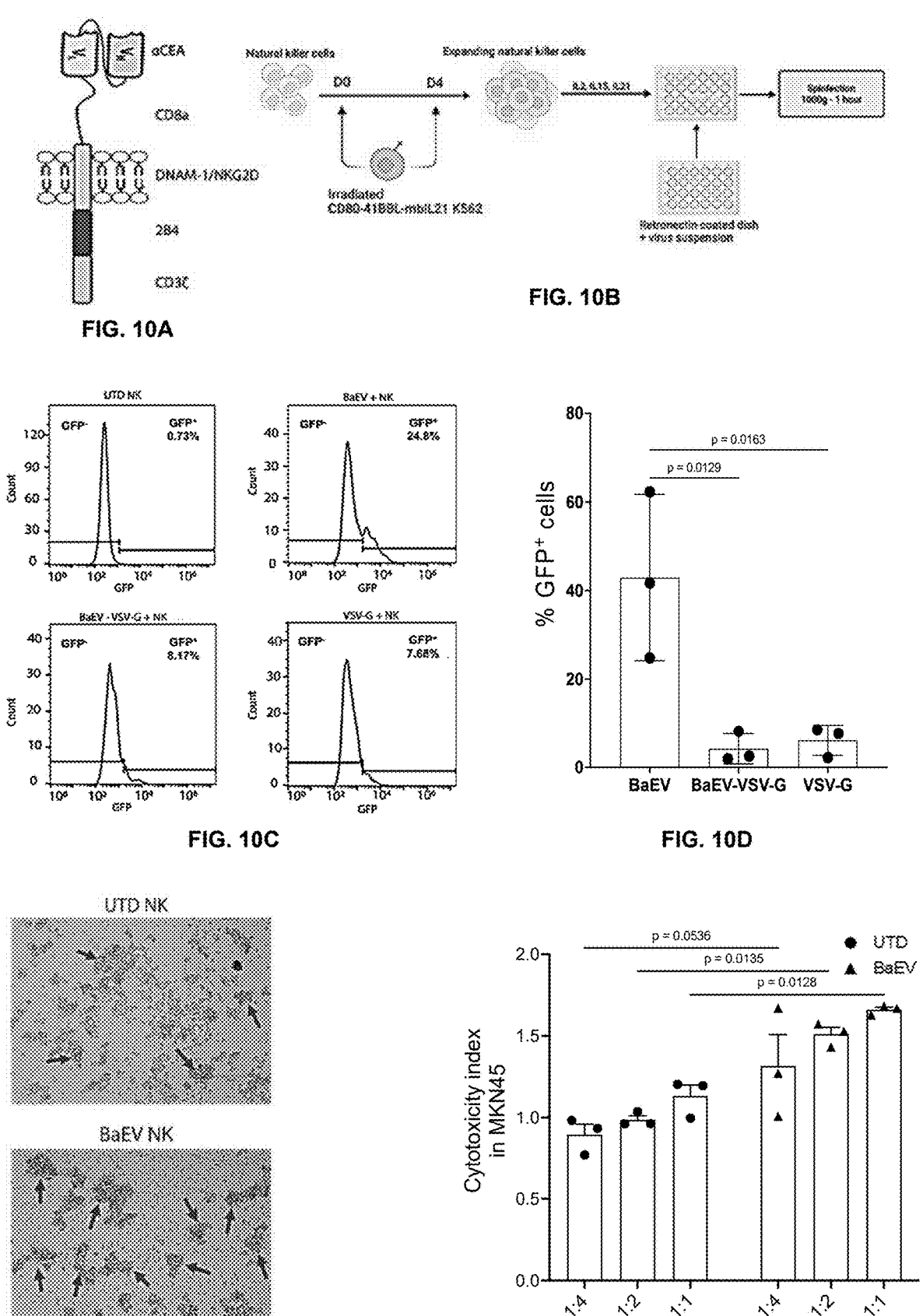
FIG. 10A is graph illustrating a chimeric antigen receptor (CAR) construct targeting carcinoembryonic antigen (CEA) according to an embodiment of the present invention.
FIG. 10B is graph illustrating the transduced CD80-41BBL-mbIL21-K562 cell-expanded NK cells with a chimeric antigen receptor (CAR) construct targeting carcinoembryonic antigen (CEA) packaged in lentiviruses pseudotyped with BaEV, VSV-G, or a combination of both.
FIG. 10C is a graph illustrating the GFP of transduced CD80-41BBL-mbIL21-K562 cell-expanded NK cells with a CAR construct targeting CEA packaged in lentiviruses pseudotyped with BaEV, VSV-G, or a combination of both compared to un-transduced (UTD) approach according to an embodiment of the present invention.
FIG. 10D is a graph illustrating the GFP of transduced CD80-41BBL-mbIL21-K562 cell-expanded NK cells with a CAR construct targeting CEA packaged in combination of BaEV and VSV-G compared to the BaEV-based approach according to an embodiment of the present invention.
FIG. 10E is an image illustrating density and district apoptotic morphology of MKN-45 cells co-cultured with untransduced NK cells compared to transduced cells with CAR construct regard BaEV lentivirus approach according to an embodiment of the present invention.
FIG. 10F is a graph illustrating the cytotoxicity index of MKN-45 cells co-cultured with CAR-NK cells compared to untransduced NK cells according to an embodiment of the present invention.

Refer to the proof results the BaEV-pseudotyped lentivirus enhanced transduction efficiency in expanding cord blood-derived NK cells compared to the VSV-pseudotyped lentivirus, including:

(i') To expand the therapeutic potential of NK cells co-cultured with CD80-41BBL-mbIL21 feeder cells, we genetically engineered them to express a chimeric antigen receptor (CAR) targeting carcinoembryonic antigen (CEA). Then, we transduced CD80-41BBL-mbIL21-K562 cell-expanded NK cells with a CAR construct targeting CEA (as shown in FIG. 10A) packaged in lentiviruses pseudotyped with BaEV, VSV-G, or a combination of both (as shown in FIG. 10B) to determine the most efficient virus. Evaluation of CAR construct expression through the GFP reporter gene at 5 days post-transduction revealed BaEV lentivirus to be more effective in NK cell transduction, with efficiencies ranging from 24%-60% across different donors (as shown in FIG. 10C). However, the combination of BaEV and VSV-G did not improve transduction efficiency in cord blood-derived NK cells compared to the BaEV-based approach, often yielding a transduction rate of lower than 10% (as shown in FIG. 10D).

Figure 11:
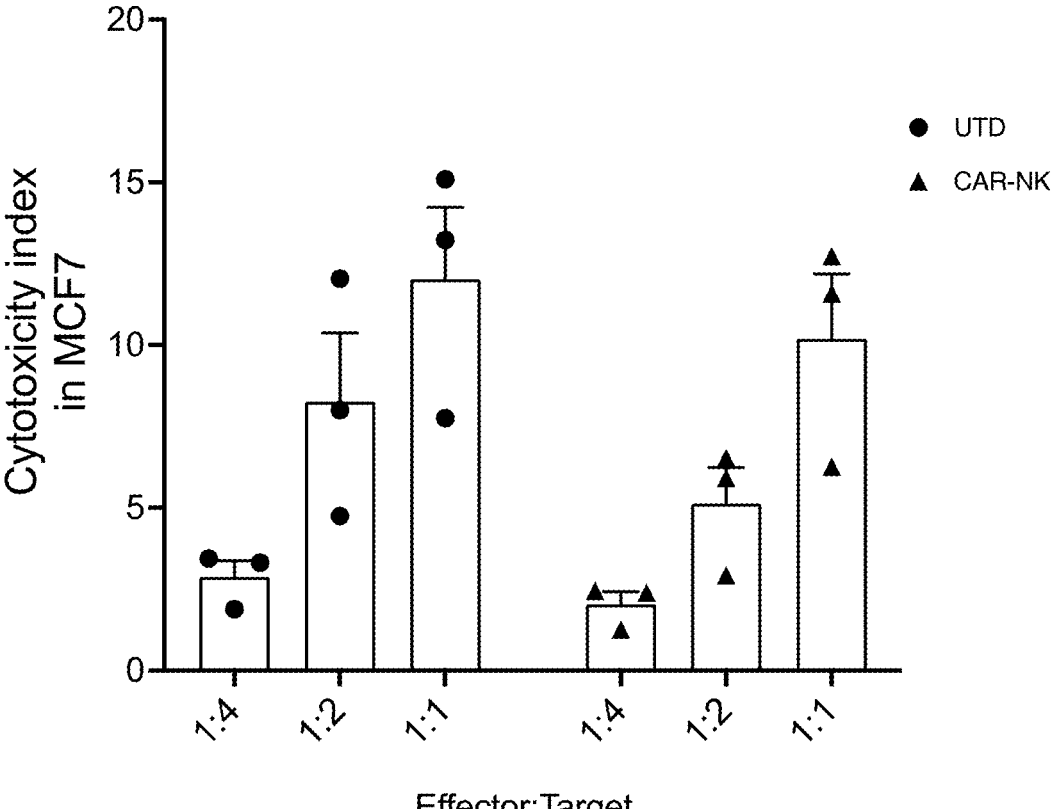
FIG. 11 is a graph illustrating the cytotoxicity index of MCF7 cells co-cultured with CAR-NK cells compared to untransduced NK cells according to an embodiment of the present invention.

(ii') Assessing the cytolytic activity of NK cells following transduction with BaEV-pseudotyped lentivirus by co-culturing them with by co-culturing them with two target cell lines: the gastric cancer cell line MKN-45 exhibits high CEA expression, and the breast cancer cell line MCF-7 lacks CEA expression; in which results including:

(a''') microscopic observation revealed reduced density and district apoptotic morphology of MKN-45 cells co-cultured with untransduced NK cells which were more pronounced in those transduced with CAR construct regard BaEV lentivirus used (as shown in FIG. 10E);

(b''') quantification analysis by flow cytometry demonstrated a dose-dependent reduction in MKN-45 cell viability upon co-culture with CAR-NK cells, but not with untransduced NK cells (as shown in FIG. 10F); and (c''') otherwise this effect was not observed in co-cultures of CAR-NK cells with MCF-7 cells, which do not express the CAR target CEA. These results suggest that the specific cytolysis is driven by the expression of the CEA-targeting CAR construct (as shown in FIG. 11).

Refer to the proof results the CAR-NK cells displayed higher cytolytic activity and superior infiltration capacity than CAR– T cells through a cytotoxicity assay against MKN-45 cells, which exhibit high levels of CEA. NK cells and T cells were transduced with lentivirus packaged with CAR constructs. Subsequently, CAR-expressing NK or T cells were isolated via cell sorting. NK and T cells, both un-transduced (UTD) and CAR-expressing (CAR), were co-cultured with labeled MKN-45 cells at an identical E:T ratio for 5 hours and then analyzed for viability.

(A2) Materials:

(aa) Prepare the CAR NK cells:

NK cell expansion was conducted using K562-CD80-41BBL-mbIL21 cells at a 1:2 ratio for 5 days in AIM-V™ medium supplemented with 10% FBS, 200 IU/ml IL-2.

Subsequently, restimulation was carried out with K562-CD80-41BBL-mbIL21 cells at a 1:1 ratio for 2 days before the transduction process with CAR-lentivirus.

The transduction of NK cells occurred on 24-well plates precoated overnight at 4° C. with RetroNectin® (Takara Bio, USA) at 5 μg/cm².

On the transduction day, lentiviral supernatant was introduced into the wells and centrifuged at 2000 g for 1.5 hours at 4° C. before adding NK cells.

Cells underwent centrifugation at 1000×g for 1 hour at 32° C.

Post-transduction, the medium was refreshed the following day and subsequently every 3 days, with CAR expression assessment performed 5 days after transduction.

(bb) Spheroid formation:

MKN-45 cells were cultured in 10-cm culture dishes using RPMI 1640 medium supplemented with 10% FBS and 1% penicillin-streptomycin.

Upon reaching confluency, cells were trypsinized and suspended in serum-free RPMI 1640 medium supplemented with MaxGel (Sigma-Aldrich, USA) at a 1:100 ratio, along with 100 ng/ml EGF and 20 ng/ml FGF.

The parental cells were then seeded at a concentration of 1000 cells per well, with 100 μl per well, in an ultra-low attachment plate sourced from Corning (USA).

Labeled effector cells (NK/T cells) were incubated with the spheroids for 48 hours. After that, the spheroids were washed and trypsinized.

Then, suspended cells were analyzed by flow cytometry.

The percentage of the effector cells detected was the percentage of infiltration.

(cc) Spheroid infiltration and cell death induced by immune cells:

T cells and NK cells were washed with PBS then resuspended in AIM-V™ 10% FBS.

Each spheroid was co-cultured with 104 immune cells for 48 hours, then the cells were collected, trypsinized, and stained with either anti-CD3 or anti-CD56 antibodies to quantify T cell and NK cell infiltration.

Cell death was assessed by staining with Zombie Red fixable viability dye (Biolegend, USA).

T cell and NK cell infiltration was measured by the percentage of CD3+ Zombie– or CD56+ Zombie– cells in total cells.

Cell death was quantified by the percentage of CD3– Zombie+ or CD56– Zombie+ cells in total cells.

Figures 12A, 12B, 12C, 12D, 12E, 12F:
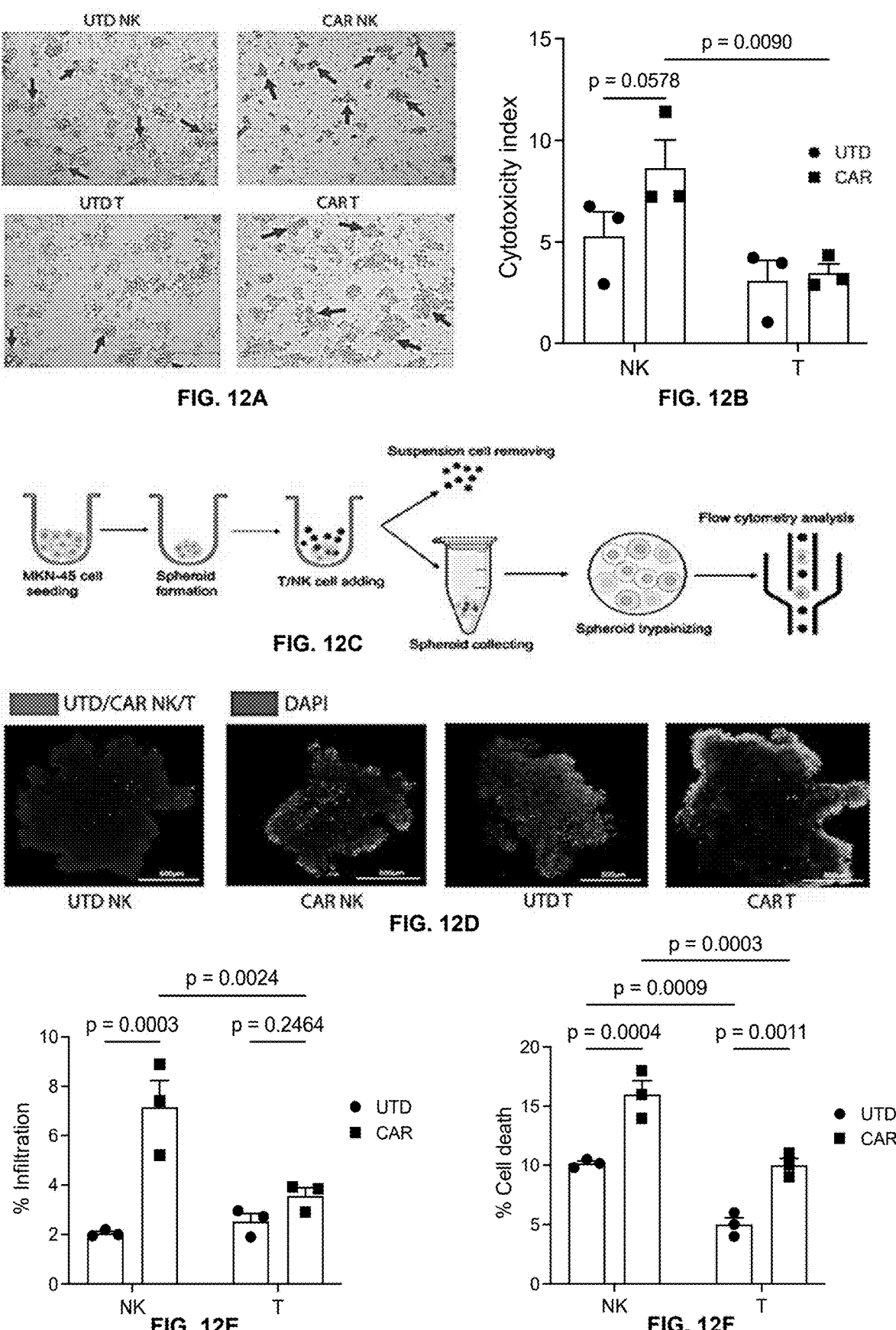
FIG. 12A is an image illustrating density and district apoptotic of NK and T cells, both un-transduced (UTD) and CAR-expressing (CAR) according to an embodiment of the present invention.
FIG. 12B is a graph illustrating the cytotoxicity index of NK and T cells, both un-transduced (UTD) and CAR-expressing (CAR) according to an embodiment of the present invention.
FIG. 12C is an image illustrating developed MKN-45 spheroid models approach according to an embodiment of the present invention.
FIG. 12D is an image illustrating infiltration of NK and T cells, both un-transduced (UTD) and CAR-expressing (CAR) according to an embodiment of the present invention.
FIG. 12E is a graph illustrating the infiltration percentage (% infiltration) of NK and T cells, both un-transduced (UTD) and CAR-expressing (CAR) according to an embodiment of the present invention.
FIG. 12F is a graph illustrating the dead cells percentage (% dead cells) of NK and T cells, both un-transduced (UTD) and CAR-expressing (CAR) according to an embodiment of the present invention.

(B2) Results:

(a1) MKN-45 cells displayed sporadic signs of cell shrinkage upon coculturing with un-transduced T or NK cells and exhibited more noticeably upon stimulation with CAR T or CAR NK cells (as shown in FIG. 12A).

(a2) CAR-NK cells significantly induced higher death rates in MKN-45 cells compared to CAR T cells, resulting in a higher cytotoxicity index (8.6±1.4 versus 3.5±0.4, p=0.009, as shown in FIG. 12B).

(a3) To examine whether CAR-NK cells might excel over CAR-T cells in solid tumor contexts, we developed MKN-45 spheroid models (as shown in FIG. 12C). MKN-45 spheroids were incubated with effector cells for 48 hours, then collected and stained for CD56 and CD3 to quantify infiltrating NK and T cells. NK effector cells exhibited superior infiltration compared to T cells, with the highest infiltration rate observed in co-culture with CAR-NK cells (7.2±1.1 versus 3.3±0.3, p=0.0024, as shown in FIG. 12D and FIG. 12E).

(a4) Assessing effector cell cytotoxicity, we stained trypsinized spheroids with a viability dye and gated on the CD56– and CD3– population. Corresponding with the infiltration trend, co-culture of MKN-45 spheroids with NK cells resulted in a significantly higher cell death rate compared to T cell effector, with the highest rate achieved with CAR-NK cells (40±2.1 versus 10±1.6, p=0.0222, as shown in FIG. 12F).

These findings confirm the integral functionality of trans-duced NK cells and highlight the potential of CAR-NK cells in targeting cancer cells due to their higher cytolytic effect and improved infiltration compared to T cells and CAR-T cells.

Another aspect of the present application relates to a population of natural killer cells (NK cells) generated or expanded by culturing the NK cells isolated from a cord blood sample in the presence of the modified K562 cells from the method comprising following in steps:

(i) isolating and purifying NK cells from a cord blood sample by adopting a gradient centrifugation;

(ii) preparing a modified K562 feeder cell line having expression of factors capable of increasing the activation and proliferation of natural killer cells, wherein the factors capable of increasing activation and proliferation of natural killer cells comprising: (A) a co-stimulatory molecule includes CD80, and 4-1BBL; and (B) a cytokine is membrane-bound IL-21 (mbIL-21); and (iii) generating or expanding the population of NK cells by culturing the NK cells isolated at step (i) in the presence of a modified K562 cell at step (ii) for 14 days.

According to the preferred embodiment of the invention, step (i) is performed similarly to step 210 according to method 200 described in detail above.

According to the preferred embodiment of the invention, step (ii) the modified K562 feeder cells co-expressing CD80, 41BBL, and mbIL-21 which are prepared according to the method 100 has been described in detail above.

According to the preferred embodiment of the invention, step (iii) is performed similarly to step 230 according to method 200 described in detail above.

Another aspect of the present application relates to a method of treating or preventing a disease or cancer or disorder through administering the population of natural killer cells in a subject, comprising steps (A1) to (C1):

(A1) isolating and purifying natural killer (NK) cells from cord blood of a subject;

(B1) generating or expanding a population of NK cells by culturing the NK cells isolated at step (A1) in the presence of a modified K562 cell for 14 days, in which the modified K562 feeder cells co-expressing CD80, 41BBL, and mbIL-21 which are prepared according to the method 100 has been described in detail above; and (C1) administering the population of NK cells generated or expanded at step (B1) to a subject.

According to the preferred embodiment of the invention, step (A1) is performed similarly to step 210 according to method 200 described in detail above.

According to the preferred embodiment of the invention, step (B1) is performed similarly to step 230 according to method 200 described in detail above.

In the embodiment of the present invention, the method of treating or preventing a disease or cancer or disorder further comprises mixing the population of NK cells with a pharmaceutically acceptable carrier.

In the embodiment of the present invention, the method of treating or preventing a disease or cancer or disorder further comprises administering at least a second therapeutic agent, in which the second therapeutic agent comprises chemotherapy, immunotherapy, surgery, radiotherapy, or biotherapy.

In the embodiment of the present invention, the disorder is an NK cell dysfunctional disorder.

In the embodiment of the present invention, the cancer is selected from the group consisting of: colon cancer, colon carcinoma, colorectal cancer, nasopharyngeal carcinoma, cervical carcinoma, oropharyngeal carcinoma, gastric carcinoma, hepatocellular carcinoma, head and neck cancer, head and neck squamous cell carcinoma (HNSCC), oral cancer, laryngeal cancer, prostate cancer, lung cancer, small cell lung cancer, non-small cell lung cancer, bladder cancer, urothelial carcinoma, melanoma, advanced melanoma, renal cell carcinoma, ovarian cancer or mesothelioma.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including" when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram, or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

a cytokine which is membrane-bound interleukin-21 (mbIL-21);

wherein step (ii) comprises:

(A) producing lentiviral vectors encoding the co-stimulatory molecule combination and the cytokine; and (B) transducing K562 cells with the lentiviral vectors to obtain the modified K562 feeder cell line;

(iii) generating or expanding a population of NK cells by culturing the NK cells isolated in step (i) in the presence of irradiated cells of the modified K562 cell line from step (ii) for 14 days, wherein the culturing comprises:

co-culturing the NK cells with irradiated cells of the modified K562 feeder cell line at a feeder-to-NK cell ratio of 5:1 at day 0 in a serum-free lymphocyte culture medium supplemented with 10% fetal bovine serum (FBS) and 200 IU/ml interleukin-2 (IL-2);

enumerating the NK cells and adding irradiated cells of the modified K562 feeder cell line to the NK cells at

---

---

What is claimed is:

1. A method for generating or expanding a population of natural killer (NK) cells, comprising:

(i) isolating and purifying NK cells from a cord blood sample by gradient centrifugation;

(ii) preparing a modified K562 feeder cell line expressing factors that increase NK cell activation and proliferation;

wherein the factors that increase NK-cell activation and proliferation comprise:

a co-stimulatory molecule combination which is CD80 and 4-1BB ligand (4-1BBL); and day 7 to maintain a feeder-to-NK cell ratio of 5:1 in a fresh serum-free lymphocyte culture medium supplemented with 10% FBS and 200 IU/ml IL-2;

after that performing lentiviral chimeric antigen receptor (CAR) transduction of the NK cells at day 7, and culturing the post transduction NK cells in the fresh serum-free lymphocyte culture medium supplemented with 10% FBS and 200 IU/ml IL-2:

replacing the culture medium with the fresh serum-free lymphocyte culture medium supplemented with 10% FBS and 200 IU/ml IL-2 at day 8;

enumerating the NK cells and adding irradiated cells of the modified K562 feeder cell line to the NK cells at day 10 to establish a feeder-to-NK cell ratio of 1:1 in the fresh serum-free lymphocyte culture medium supplemented with 10% FBS, and 200 IU/ml IL-2; and collecting the population of NK cells at day 14; wherein the population of NK cells is functionally competent to exhibit high cytotoxic activity.

2. A population of natural killer (NK) cells exhibiting enhanced cytotoxic activity relative to NK cells expanded without a modified K562 feeder cell line expressing CD80, 4-1BB ligand (4-1BBL), and membrane-bound interleukin-21 (mbIL-21), and without defined temporal modulation of feeder-to-NK cell ratios; wherein the population of NK cells is generated or expanded by a method comprising:

(i) isolating and purifying NK cells from a cord blood sample by gradient centrifugation;

(ii) preparing a modified K562 feeder cell line expressing factors that increase NK cell activation and proliferation;

wherein the factors that increase NK-cell activation and proliferation comprise:

a co-stimulatory molecule combination which is CD80 and 4-1BB ligand (4-1BBL); and a cytokine which is membrane-bound interleukin-21 (mbIL-21);

wherein step (ii) comprises:

(A) producing lentiviral vectors encoding the co-stimulatory molecule combination and the cytokine; and (B) transducing K562 cells with the lentiviral vectors to obtain the modified K562 feeder cell line;

(iii) generating or expanding a population of NK cells by culturing the NK cells isolated in step (i) in the presence of irradiated cells of the modified K562 cell line from step (ii) for 14 days, wherein the culturing comprises:

co-culturing the NK cells with irradiated cells of the modified K562 feeder cell line at a feeder-to-NK cell ratio of 5:1 at day 0 in a serum-free lymphocyte culture medium supplemented with 10% fetal bovine serum (FBS) and 200 IU/ml interleukin-2 (IL-2);

enumerating the NK cells and adding irradiated cells of the modified K562 feeder cell line to the NK cells at day 7 to maintain a feeder-to-NK cell ratio of 5:1 in a fresh serum-free lymphocyte culture medium supplemented with 10% FBS and 200 IU/ml IL-2;

after that performing lentiviral chimeric antigen receptor (CAR) transduction of the NK cells at day 7, and culturing the post transduction NK cells in the fresh serum-free lymphocyte culture medium supplemented with 10% FBS and 200 IU/ml IL-2;

replacing the culture medium with the fresh serum-free lymphocyte culture medium supplemented with 10% FBS and 200 IU/ml IL-2 at day 8;

enumerating the NK cells and adding irradiated cells of the modified K562 feeder cell line to the NK cells at day 10 to establish a feeder-to-NK cell ratio of 1:1 in the fresh serum-free lymphocyte culture medium supplemented with 10% FBS, and 200 IU/ml IL-2; and collecting the population of NK cells at day 14; wherein the population of NK cells is functionally competent to exhibit high cytotoxic activity.

* * * * *

SEQUENCE LISTING

```
Sequence total quantity: 3
SEQ ID NO: 1             moltype = AA  length = 254
FEATURE                  Location/Qualifiers
source                   1..254
                         mol_type = protein
                         organism = Homo sapiens
SEQUENCE: 1
MEYASDASLD PEAPWPPAPR ARACRVLPWA LVAGLLLLLL LAAACAVFLA CPWAVSGARA   60
SPGSAASPRL REGPELSPDD PAGLLDLRQG MFAQLVAQNV LLIDGPLSWY SDPGLAGVSL  120
TGGLSYKEDT KELVVAKAGV YYVFFQLELR RVVAGEGSGS VSLALHLQPL RSAAGAAALA  180
LTVDLPPASS EARNSAFGFQ GRLLHLSAGQ RLGVHLHTEA RARHAWQLTQ GATVLGLFRV  240
TPEIPAGLPS PRSE                                                    254

SEQ ID NO: 2             moltype = AA  length = 288
FEATURE                  Location/Qualifiers
source                   1..288
                         mol_type = protein
                         organism = Homo sapiens
SEQUENCE: 2
MGHTRRQGTS PSKCPYLNFF QLLVLAGLSH FCSGVIHVTK EVKEVATLSC GHNVSVEELA   60
QTRIYWQKEK KMVLTMMSGD MNIWPEYKNR TIFDITNNLS IVILALRPSD EGTYECVVLK  120
YEKDAFKREH LAEVTLSVKA DFPTPSISDF EIPTSNIRRI ICSTSGGFPE PHLSWLENGE  180
ELNAINTTVS QDPETELYAV SSKLDFNMTT NHSFMCLIKY GHLRVNQTFN WNTTKQEHFP  240
DNLLPSWAIT LISVNGIFVI CCLTYCFAPR CRERRRNERL RRESVRPV               288

SEQ ID NO: 3             moltype = AA  length = 287
FEATURE                  Location/Qualifiers
source                   1..287
                         mol_type = protein
                         organism = Homo sapiens
SEQUENCE: 3
MWLQSLLLLG TVACSISMRS SPGNMERIVI CLMVIFLGTL VHKSSSQGQD RHMIRMRQLI   60
DIVDQLKNYV NDLVPEFLPA PEDVETNCEW SAFSCFQKAQ LKSANTGNNE RIINVSIKKL  120
KRKPPSTNAG RRQKHRLTCP SCDSYEKKPP KEFLERFKSL LQKMIHQHLS SRTHGSEDSE  180
QKLISEEDLA LSNSIMYFSH FVPVFLPAKP TTTPAPRPPT PAPTIASQPL SLRPEASRPA  240
AGGAVHTRGL DKPFWVLVVV GGVLACYSLL VTVAFIIFWV RSKRSRP               287
```